United States Patent [19]

Salvadori

[11] 4,363,406

[45] Dec. 14, 1982

[54] FLUID DRAINAGE BAG WITH TEAR TAB DRAIN

[75] Inventor: Lawrence A. Salvadori, Milwaukee, Wis.

[73] Assignee: Plastronics, Inc., Milwaukee, Wis.

[21] Appl. No.: 254,909

[22] Filed: Apr. 16, 1981

Related U.S. Application Data

[63] Continuation of Ser. No. 58,067, Jul. 16, 1979, abandoned.

[51] Int. Cl.³ .................. B65D 33/02; B65D 33/00
[52] U.S. Cl. ........................................ 206/604; 206/628
[58] Field of Search .............. 206/604, 628, 620, 484, 206/633; 128/295, 272, DIG. 24

[56] References Cited

U.S. PATENT DOCUMENTS

| | | | |
|---|---|---|---|
| 3,270,790 | 9/1966 | Clark | 128/DIG. 24 |
| 3,516,537 | 6/1970 | Dreyfus et al. | 206/633 |
| 3,939,969 | 2/1976 | Miller et al. | 206/633 |

FOREIGN PATENT DOCUMENTS 61695  5/1955  France ................ 206/628

Primary Examiner—Stephen P. Garbe
Attorney, Agent, or Firm—Michael, Best & Friedrich

[57] ABSTRACT

A fluid drainage bag comprises a sealed bag body and a tab member integrally formed on the bag body. When the tab member is laterally pulled away from the bag body by the attendant, the bag body tears to form a permanent outlet opening through which fluid may be drained from the bag body.

5 Claims, 6 Drawing Figures

U.S. Patent Dec. 14, 1982 4,363,406
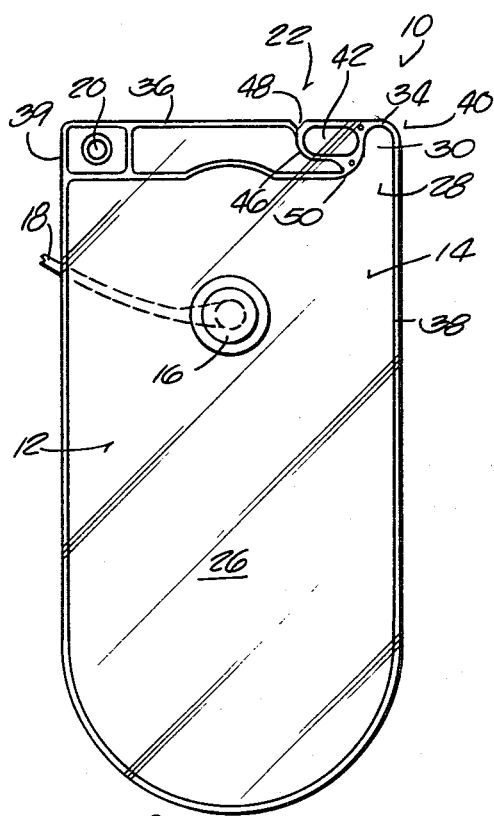
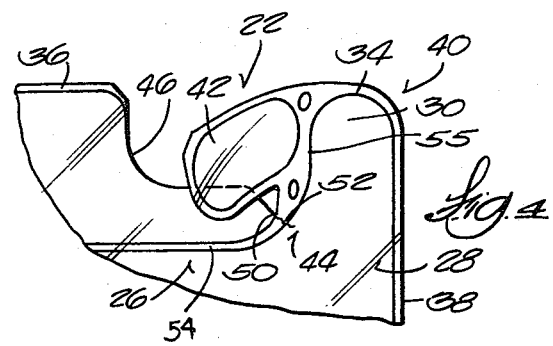
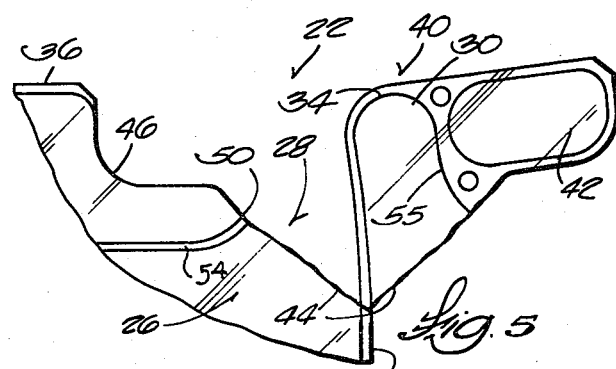
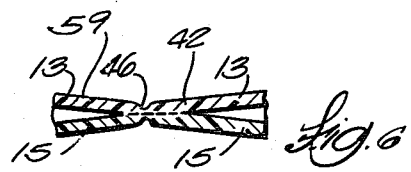
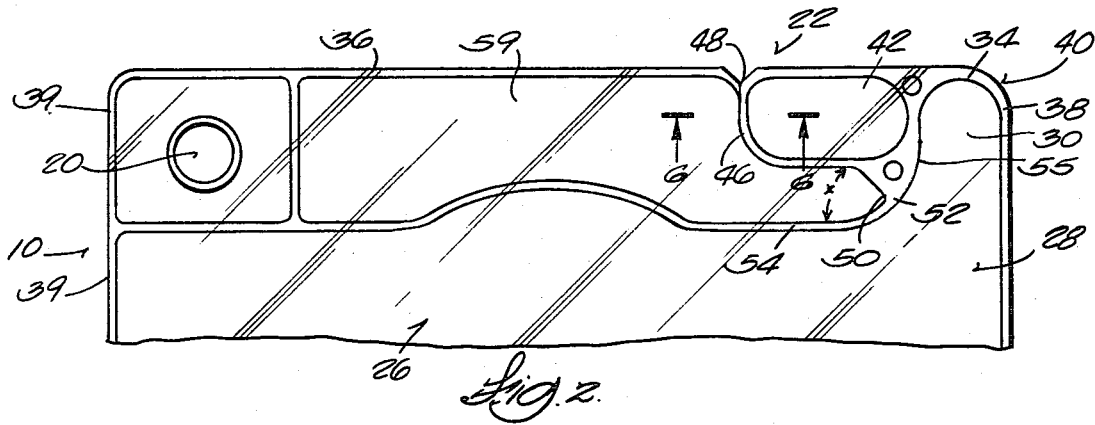
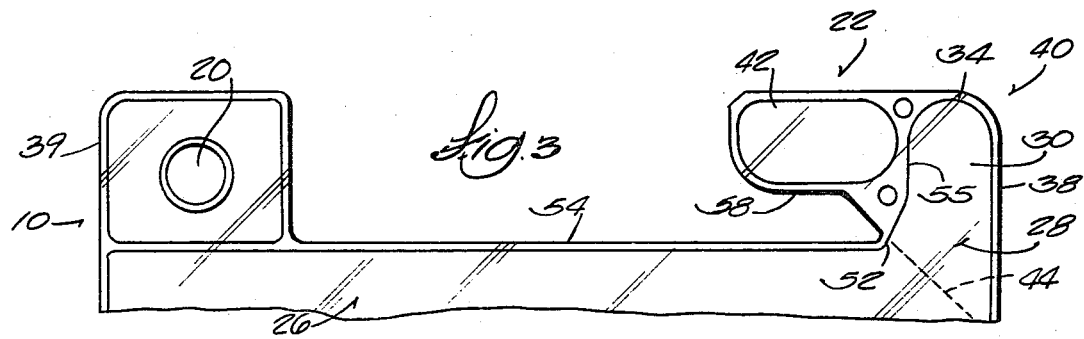

FLUID DRAINAGE BAG WITH TEAR TAB DRAIN

This is a continuation of application Ser. No. 058,067 filed July 16, 1979, now abandoned.

FIELD OF THE INVENTION

The invention generally relates to fluid drainage bags. More particularly, this invention relates to disposable fluid drainage bags.

DESCRIPTION OF THE PRIOR ART

Fluid drainage bags are widely used to collect fluid from a bedridden patient. In this and related applications, the bags are often used only a single time and are thereafter drained and discarded. It is neither pracitcal nor economical to use conventional fluid drainage bags having relatively costly and elaborate drainage valve assemblies in situations which call for one-time use of the bags.

SUMMARY OF THE INVENTION

The invention provides a fluid drainage bag which is particularly adapted for use in situations where one-time use of the bag is envisioned. The bag comprises a bag body and means for defining within the bag body an internal fluid chamber having an inlet port. Opening means is integrally formed on the bag body for tearing away a preselected portion of the bag body to form a permanent outlet opening in the internal fluid chamber through which fluid accumulated in the internal chamber may be drained from the bag without the use of any other associated drain assemblies.

BRIEF DESCRIPTION OF THE DRAWINGS

FIG. 1 is a front elevation view of a fluid drainage bag having a tear-away tab which opens a permanent drain outlet opening in the bag;

FIG. 2 is an exploded view of the top edge of the bag shown in FIG. 1;

FIG. 3 is an exploded view of the top edge of a fluid drainage bag having a tear-away tab of alternate construction to that shown in FIGS. 1 and 2;

FIGS. 4 and 5 are fragmentary exploded views of the tear-away drain tab shown in FIGS. 1 and 2 as it is being pulled laterally away from the bag to open the permanent outlet opening in the bag; and FIG. 6 is a sectional view of the seam which forms a preformed portion of the tear line taken generally along line 6—6 of FIG. 2.

DESCRIPTION OF THE PREFERRED EMBODIMENT

A fluid drainage bag 10 is shown in FIG. 1. The invention perhaps finds its widest application in connection with disposable fluid drainage bags which are typically used in bedside urinary collection systems or the like. While the invention will hereafter be discussed in that environment, it should be appreciated that the fluid drainage bag is applicable for use in other environments.

The body 12 of the bag 10 is preferably formed of two overlapping sheets 13 and 15 of polyvinyl chloride plastic (see FIG. 6). An internal fluid chamber 14 is formed within the bag body 12 by suitable means, such as electronic welding, which joins the peripheral edges of the overlapping sheets together. An inlet fitting 16 defining an inlet port communicates with the internal chamber 14, and a flexible inlet tube 18 (shown in phantom lines in FIG. 1), typically also of polyvinyl chloride material, is connected at one end to the patient and at the opposite end to the inlet fitting 16 so that fluid may be conducted from the patient into the internal fluid chamber 14. A hole 20 is formed in the bag body 12 to permit hanging of the bag 10 near the patient.

In accordance with the invention, opening means 22 is integrally attached to the bag body 12 for forming a tear in the polyvinyl chloride material of the bag body 12 to open a permanent outlet passage (see FIGS. 4 and 5) in the internal fluid chamber 14 through which fluid may be drained from the bag 10. After drainage, the bag 10 is then discarded.

While the bag 10 having integral opening means 22 may be variously constructed, in the illustrated embodiment the internal fluid chmaber 14 is formed so as to include a main body portion 26 having an outlet port 28 which is normally sealed within the confines of the bag body 12. More particularly, a truncated outlet extension portion 30 is formed within the confines of the bag body 12. The outlet extension 30 extends from the outlet port 28 and has a sealed end 34 which is spaced from the outlet port 28. As will soon be described, the opening means 22 is operative for tearing the bag body 12 to separate the outlet extension 30 from the outlet port 28 to thereby open the outlet port 28 to permit drainage of the fluid from the main body portion 26 of the internal fluid chamber 14.

The material of sheets 13 and 15 in the area of outlet port 28 at the base of outlet extension 30 is not weakened by a score line or similar means to maintain the sealed integrity of the outlet extensions until the tearing operation is performed.

While the outlet port 28 and associated outlet extension 30 may be variously located on the bag body 12, in the preferred embodiment shown in FIGS. 1, 2, 4, 5 and 6, the bag body 12 includes seams 36, 38 and 39 which define, respectively, the top peripheral edge and the opposite peripheral side edges of the bag 10. Another seam 54 extends from the side seam 39 in a path below and generally parallel to the top edge seam 36, and generally defines the uppermost extent of the main body portion 26 of the internal fluid chamber 14. Seam 54 terminates in a spaced relationship from the side seam 38, and seam 55 thereafter extends in a generally upwardly sloping path from seam 54 until the top edge seam 36 is joined. By virtue of this construction, the confines of the outlet extension 30, the outlet port 28, and the sealed end 34 of the outlet extension 30 are defined within a corner section 40 of the bag 10.

Also by virtue of this construction, an upper portion 59 of the bag body 12 is formed, being isolated from communication with the interior fluid chamber 14 by the seams 54 and 55. The opening means 22 includes a tap member 42 which is integrally formed on the upper portion 59 adjacent to seam 55.

More particularly, a portion of the upper portion 59 is crimped (see FIG. 6), such as by electronic welding. This crimping weakens the polyvinyl chloride material to form a preformed tear seam 46. As is best shown in FIGS. 1 and 2, the preformed tear seam 46 extends between a first tearing edge 48 (see FIG. 2) which intersects the top edge seam 36 and a second tearing edge 50 which joins seam 55. The tab member 42 is thereby defined intermediate the preformed tear seam 46, the top edge seam 36, and seam 55 and normally occupies a coplanar relationship with the upper portion 59 of the bag body 12.

By grasping the tab member 42 between one's thumb and forefinger and then pulling the tab member 42 laterally toward the side edge seam 38, the bag body 12 tears along the preformed tear seam 46. The tab member 42 is thereby lifted away from its coplanar relationship with the bag body 12 (see FIG. 4). The second tearing edge 50 thereafter acts as a stress point 52 which, as the tab member 42 is progressively pulled laterally toward the side edge seam 38, breaks the seam 55 and initiates a tear line 44 (see FIG. 5) which proceeds from the second tearing edge 50 across the outlet extension 30 until the side edge seam 38 of the bag 10 is reached. At this point, the tab member 42 has separated the entire corner section 40 from the bag body 12 and, in doing so, has separated the outlet extension 30 from the outlet port 28. A permanent drain opening is thus formed through which fluid may be drained from the bag 10.

To guide and otherwise facilitate this tearing action occasioned by laterally pulling upon the tab member 42, the second tearing edge 50 joins seam 55 at an angle (designated as angle x in FIG. 2) which is measured between the seam line 54 and the preformed tear seam 46 immediately adjacent to the second tearing edge 50. By virtue of this angle, the action of the stress point 52 in breaking the seam 55 and initiating the tear line 44 across the outlet extension 30 is enhanced. Furthermore, the tear line 44 thereafter proceeds from the stress point 52 across the outlet extension 30 at generally the same angle to increase the size of the drain opening formed. While this angle may be varied, in the preferred embodiment, the angle is approximately 45°.

Additionally, the width of the seam 55 is increased immediately above the juncture of the second tearing edge 50 and the seam 55 to thereby strengthen the seam 55 at this point. The reinforcement of the seam 55 at this point directs the tearing action at the stress point 52 away from the path of seam 55 and into the outlet extension 30. Thus, undesired tearing along the path of seam 55 is prevented.

It should be appreciated that the particular construction of the preferred embodiment protects the tab member 42 from being accidentally ruptured or damaged during the manufacturing process. More particularly, during the manufacturing process the two sheets 13 and 15 of polyvinyl chloride material are electronically welded together forming the seams 36, 38, 39, 54 and 55 and resulting in the presence of excess polyvinyl chloride material extending outwardly from the peripheral seams 36, 38 and 39. This excess material is usually removed by cutting or tearing. By shielding the major portion of the tab member 42 within the confines of the upper portion 59, the tab member 42 is protected against accidental tearing or damage during removal of this excess material.

A second embodiment is shown in FIG. 3. In this embodiment, and unlike the first described embodiment, most of the upper portion 59 of the bag body 12 is removed during the manufacturing process so that the tab member 42 forms a "free standing" appendage which extends outwardly from the corner section 40 of the bag body 12 away from the side edge seam 38. However, like the first described embodiment, the underbody portion 58 of the tab member 42 joins the seam 55 at an angle, and the portion of seam 55 immediately above this juncture is reinforced. The juncture thus serves as the stress point 52 which breaks seam 55 and initiates tearing across the outlet extension 30 in identical fashion to that illustrated in FIGS. 4 and 5 (and as is shown in phantom lines in FIG. 3). The sealed end portion 34 of the outlet extension 30 is thereby separated from the outlet port 28, forming the permanent drainage outlet.

Although but two embodiments of the present invention have been illustrated and described, it will be apparent to those skilled in the art that various exchanges and modifications may be made therein without departing from the spirit of the invention or from the scope of the appended claims.

I claim:

1. A fluid drainage bag comprising:
   a bag body including a top edge and an adjoining side edge, said top edge and said adjoining side edge together defining a corner section of said bag body;
   an internal fluid chamber within said bag body having an inlet port and an outlet port;
   an outlet extension portion communicating with said outlet port and having a sealed end portion spaced from said outlet port, said outlet extension portion located within said corner section of said bag body, the material of said outlet extension portion in the area of said outlet port is not weakened by a score line or similar means;
   a seam in said corner section defining a preformed section of a tear line extending from said top edge of said bag body toward said outlet extension portion;
   a tab member formed intermediate said seam and said top edge of said bag body, said tear tab adapted when initially pulled laterally toward said outlet extension portion to cause the bag body to tear along said preformed tear seam and further adapted when pulled further to cause the bag body to tear across the previously unweakened material of said outlet extension portion to thereby create an opening at said outlet port to facilitate drainage of fluid from said internal fluid chamber within said bag body.

2. A fluid drainage bag according to claim 1
   wherein said preformed section of said tear line has a first tearing edge intersecting said top edge of said bag body, and
   a second tearing edge located adjacent said outlet extension portion at the point said outlet extension portion will begin to tear when said tear tab is pulled further.

3. A fluid drainage bag according to claim 2 wherein said second tearing edge is adapted to extend into said outlet extension portion such that the extension of said second tearing edge initiates tearing across said outlet extension portion at an angle away from said sealed end portion thereof.

4. A fluid drainage bag according to claim 3 wherein said angle is approximately 45° from horizontal.

5. A fluid drainage bag comprising:
   a bag body having an internal fluid chamber therein, said internal chamber having an inlet port and an outlet port;
   an outlet extension portion communicating with said outlet port and having a sealed end portion spaced from said outlet port, the material of said outlet extension portion in the area of said outlet port is not weakened by a score line or similar means;
   a tear tab having a free edge formed integral with one edge of said outlet extension portion, a seam extending along the juncture between said tear tab and said outlet extension portion, said free edge of said tear tab intersecting said seam at a stress point, said seam adjacent said stress point being reinforced so that when said tear tab is pulled laterally toward said outlet extension portion it will cause the bag body to tear across the previously unweakened material of said outlet extension portion to thereby create an opening at said outlet port to facilitate drainage of fluid from said internal fluid chamber within said bag body.

* * * * *

UNITED STATES PATENT AND TRADEMARK OFFICE
CERTIFICATE OF CORRECTION

PATENT NO. : 4,363,406
DATED : December 14, 1982
INVENTOR(S) : Lawrence A. Salvadori It is certified that error appears in the above—identified patent and that said Letters Patent is hereby corrected as shown below:

Column 1, Line 16, Delete "pracitcal" and substitute therefor ---practical---

Column 3, Line 13, After "the" and before "outlet" insert -- the previously unweakened base of --

Signed and Sealed this

Twenty-fifth Day of October 1983

[SEAL]

Attest:

GERALD J. MOSSINGHOFF

Attesting Officer

Commissioner of Patents and Trademarks